United States Patent [19]

Buzzetti et al.

[11] Patent Number: 4,810,423
[45] Date of Patent: Mar. 7, 1989

[54] 1,2-BETA-METHYLENE-4-SUBSTITUTED ANDROSTENE-3,17-DIONE DERIVATIVES AND PROCESS FOR THEIR PREPARATION

[75] Inventors: Franco Buzzetti, Monza; Enrico di Salle; Paolo Lombardi, both of Milan, all of Italy

[73] Assignee: Farmitalia Carlo Erba S. R. L., Milan, Italy

[21] Appl. No.: 86,607

[22] Filed: Aug. 18, 1987

[30] Foreign Application Priority Data

Oct. 9, 1986 [GB] United Kingdom ............... 8624251

[51] Int. Cl.$^4$ ............... C07J 1/100; A61K 31/56; C07C 117/00
[52] U.S. Cl. .................. 260/397.4; 260/349; 514/178
[58] Field of Search ........... 260/397.3, 397.4, 397.5; 514/177, 178

[56] References Cited

U.S. PATENT DOCUMENTS

| 1,087,782 | 10/1967 | Schering | 260/397 |
| 2,744,120 | 5/1956 | Fried et al. | |
| 4,071,625 | 1/1978 | Grunwell et al. | 514/172 |
| 4,235,893 | 11/1980 | Brodie et al. | |
| 4,289,762 | 9/1981 | Metcalf et al. | 514/179 |
| 4,322,406 | 3/1982 | Debono et al. | 424/118 |

FOREIGN PATENT DOCUMENTS

| 759886 | 6/1971 | Belgium . |
| 816364 | 12/1974 | Belgium . |
| 3422187 | 10/1985 | Denmark . |
| 100566A | 2/1984 | European Pat. Off. . |
| 210832A | 2/1987 | European Pat. Off. . |
| 6503784 | 9/1965 | Netherlands . |
| 1042291 | 9/1966 | United Kingdom . |
| 2100601 | 5/1981 | United Kingdom . |

OTHER PUBLICATIONS

Covey, et al., "A New Hypothesis Based on ... " Cancer Research (Suppl) 42,3327s-3333s, Aug. 1982.
Brodie, "Overview of Recent ... " Cancer Research (Suppl) 42, 3312s-3314s, Aug. 1982.
Metcalf, et al., "Substrate-Induced Inactivation ... " J. Am. Chem. Soc., 1981, 103, 3221-3222.
100:96848q, "Prostatic Cancer ... " Chem. Abstracts vol. 100, 1984.
Marsh, D. A. et al., "Aromatase Inhibitors, Synthesis . . . " J. Med. Chemistry, 1985, 28, pp. 788-795.

Primary Examiner—H. M. S. Sneed
Assistant Examiner—J. Saba
Attorney, Agent, or Firm—Armstrong, Nikaido Marmelstein & Kubovcik

[57] ABSTRACT

The invention relates to new aromatase inhibitor agents having the general formula (I)

wherein $R_1$ is hydrogen or a group $=CHR_3$ wherein $R_3$ is hydrogen or $C_1$–$C_6$ alkyl; the symbol $=\!=\!=$ indicates the presence of a single or double bond in such a way that, when $R_1$ is hydrogen, (a) is single bond and (b) is either single or double bond, while, when $R_1$ is a group $=CHR_3$ as defined above, (a) is double bond and (b) is single bond; $R_2$ is hydrogen or fluorine; and R is (1) a group —$OR_4$ wherein $R_4$ is
 (a) hydrogen;
 (b) $C_1$–$C_6$ alkyl;
 (c) a phenyl or benzyl group, each unsubstituted or ring-substituted by one or more substituents chosen from $C_1$–$C_4$ alkyl, halogen, trifluoromethyl, nitro, amino, hydroxy and $C_1$–$C_4$ alkoxy;
 (d) a group —$COR_5$ wherein $R_5$ is
  (i) a $C_1$–$C_{22}$ saturated or $C_2$–$C_{22}$ unsaturated aliphatic hydrocarbon radical;
  (ii) a $C_4$–$C_7$ monocycloalkyl group; or
  (iii) a phenyl or benzyl group, each unsubstituted or ring substituted as reported above; or
 (e) a hydroxy protecting group;
(2) a group —$SR_6$ wherein $R_6$ either has one of the meanings (a) to (d) indicated above for $R_4$ or is a group —$SR_7$ wherein $R_7$ is
 (iv) $C_1$–$C_6$ alkyl;
 (v) a phenyl or benzyl group, each unsubstituted or ring-substituted as reported above; or
 (vi) a steroidic residue of formula wherein $R_1$, $R_2$, (a), (b) and the symbol $=\!=\!=$ are as defined above;
(3) the group —$N_3$; or
(4) a group wherein each of $R_8$ and $R_9$, independently, is hydrogen or $C_1$–$C_6$ alkyl,
and the pharmaceutically acceptable salts thereof, which are useful in therapy, in particular, as anti-cancer agents.

4 Claims, No Drawings

1,2-BETA-METHYLENE-4-SUBSTITUTED ANDROSTENE-3,17-DIONE DERIVATIVES AND PROCESS FOR THEIR PREPARATION

The present invention relates to 1,2-β-methylene-4-substituted androstene-3,17-dione derivatives, to a process for their preparation, to pharmaceutical compositions containing them, and to the use of said compounds for the treatment of hormone-dependent cancers. Basic and clinical data indicate that aromatized metabolites of androgens, i.e. the estrogens, are the hormones involved in the pathogenic cellular changes associated with the growth of some hormone-dependent cancers, e.g., breast, endometrial, ovarian and pancreatic carcinomas.

Estrogens are also involved in the pathogenesis of benign prostatic hyperplasia.

Endogenous estrogens are ultimately formed from either androstenedione or testosterone as immediate precursors.

The reaction of central importance is the aromatization of the steroidic ring A, which is performed by the enzyme aromatase. As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumours. Known steroidal substances which have been reported to be endowed with an aromatase-inhibiting action are, for example, testololactone [U.S. Pat. No. 2,744,120], 4-hydroxyandrost-4-ene-3,17-dione and esters thereof [see, for example, U.S. Pat. No. 4,235,893], 10-(1,2-propadienyl)ester-4-ene-3,17-dione [U.S. Pat. No. 4,289,762], 10-(2-propynyl)ester-4-ene-3,17-dione [J. Am. Chem. Soc., 103, 3221 (1981) and U.S. Pat. No. 4,322,416], 19-thioandrostene derivatives [Europ. Pat. Appl. No. 100566], androsta-4,6-diene-3,17-dione, androsta-1,4,6-triene-3,17-dione [G.B. Pat. Appl. No. 2,100,601A] and androsta-1,4-diene-3,17-dione [Cancer Res. (Suppl.) 42, 3327 (1982)].

The novel compounds of the present invention are potent aromatase inhibitors, by virtue of their ability to specifically inhibit estorgens synthesis.

The present invention provides compounds having the following general formula (I)

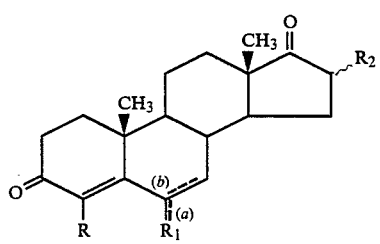

wherein $R_1$ is hydrogen or a group $=CHR_3$ wherein $R_3$ is hydrogen or $C_1$–$C_6$ alkyl; the symbol ⌇ indicates the presence of a single or double bond in such a way that, when $R_1$ is hydrogen, (a) is single bond and (b) is either single or double bond, while, when $R_1$ is a group $=CHR_3$ as defined above, (a) is double bond and (b) is single bond; $R_2$ is hydrogen or fluorine; and R is (1) a group —$OR_4$ wherein $R_4$ is
(a) hydrogen;
(b) $C_1$–$C_6$ alkyl;
(c) a phenyl or benzyl group, each unsubstituted or ring-substituted by one or more substituents chosen from $C_1$–$C_4$ alkyl, halgoen, trifluoromethyl, nitro, amino, hydroxy and $C_1$–$C_4$ alkoxy;
(d) a group —$COR_5$ wherein $R_5$ is
(i) a $C_1$–$C_{22}$ saturated or $C_2$–$C_{22}$ unsaturated aliphatic hydrocarbon radical;
(ii) a $C_4$–$C_7$ monocycloalkyl group; or
(iii) a phenyl or benzyl group, each unsubstituted or ring substituted as reported above; or
(e) a hydroxy protecting group;
(2) a group —$SR_6$ wherein $R_6$ either has one of the meanings (a) to (d) indicated above for $R_4$ or is a group —$SR_7$ wherein $R_7$ is
(iv) $C_1$–$C_6$ alkyl;
(v) a phenyl or benzyl group, each unsubstituted or ring-substituted as reported above; or
(vi) a steroidic residue of formula

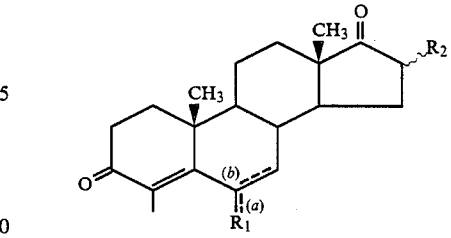

wherein $R_1$, $R_2$, (a), (b) and the symbol ⌇ are as defined above;
(3) the group —$N_3$; or
(4) a group

wherein each of $R_8$ and $R_9$, independently, is hydrogen or $C_1$–$C_6$ alkyl.

The invention includes also the pharamaceutically acceptable salts of the compounds of formula (I) containing a salifiable group.

In the formulae of this specification, a heavy solid line (◂) indicates that a substituent is in the β-configuration, i.e. above the plane of the ring, and a wavy line (∿) indicates a substituent may be either in the α-configuration, i.e. below the plane of the ring, or in the β-configuration or in both, i.e. a mixture thereof such as a racemic mixture. The formula reported above for the compounds of the invention is meant to comprise all the possible isomers of formula (I) both separately and in mixture, including, e.g., the Z and E isomers of the compounds of formula (I) in which $R_1$ is a group $=CHR_3$, wherein $R_3$ is $C_1$–$C_6$ alkyl, both separately and in mixture.

The aliphatic hydrocarbon radicals, including the alkyl groups and the aliphatic moieties of the alkoxy groups, may be branched or straight chain. A $C_1$–$C_6$ or $C_1$–$C_4$ alkyl group is, preferably, methyl or ethyl.

A halogen is, preferably, chlorine, bromine or fluorine, in particular fluorine.

A $C_1$–$C_4$ alkoxy group is, preferably, methoxy or ethoxy.

A C$_1$-C$_{22}$ saturated aliphatic hydrocarbon radical is, preferably, a C$_1$-C$_{17}$ alkyl group, in particular, e.g., methyl, ethyl, n-propyl, n-butyl, tert-butyl or the residue of a saturated fatty acid, e.g. n-undecyl, n-tridecyl, n-pentadecyl or n-heptadecyl.

A C$_2$-C$_{22}$ unsaturated aliphatic hydrocarbon radical preferably contains 2 to 17 carbon atoms e.g., allyl, or the residue of an unsaturated fatty acid, e.g., cis-or trans-8-heptadecenyl.

A C$_4$-C$_7$ monocycloalkyl group is, preferably, a C$_5$-C$_7$ monocycloalkyl, in particular cyclopentyl or cyclohexyl.

An —OR$_4$ hydroxy protected group is a group, especially an ether group, convertible to hydroxy group under mild reaction conditions, e.g. acid hydrolysis. Examples are acetalic ethers, enolethers and silylethers.

Particularly preferred hydroxy protecting groups are:

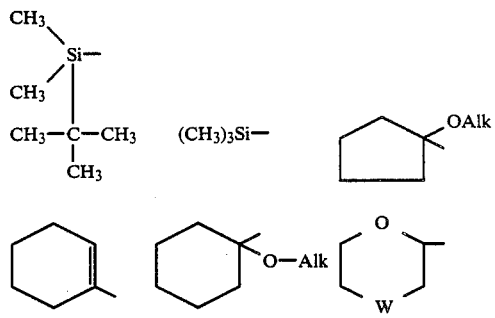

wherein W is —O— or —CH$_2$—, and Alk is a lower alkyl group more preferably, they are 2'-tetrahydropyranyl or trimethyl silyl.

When R is a group —OR$_4$ or a group —SR$_6$ wherein R$_4$ or, respectively, R$_6$ is —COR$_5$, preferably R$_5$ is a C$_1$-C$_{22}$ saturated aliphatic hydrocarbon radical, especially a C$_1$-C$_{17}$ alkyl group and in particular one of those specified before, most preferably methyl or ethyl; or a phenyl or benzyl group either unsubstituted or ring-substituted by C$_1$-C$_4$ alkyl, in particular methyl, or by a fluorine, trifluoromethyl, nitro, hydroxy, methoxy or ethoxy group.

When R is a group —OR$_4$ or a group —SR$_6$, preferably R$_4$ or, respectively, R$_6$ is hydrogen, C$_1$-C$_6$ alkyl, in particular methyl or ethyl, or a group —COR$_5$ wherein R$_5$ is C$_1$-C$_{17}$ alkyl, in particular methyl or ethyl.

When R is a group

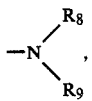

preferably each R$_8$ and R$_9$ is, independently, hydrogen or C$_1$-C$_3$ alkyl; preferred groups

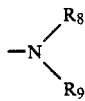

are amino, methylamino, ethylamino, dimethylamino and diethylamino, most preferably amino.

As already said, the invention includes also the pharmaceutically acceptable salts of the compounds of formula (I) containing a salifiable group.

Thus, salts according to the invention are the salts of the compounds of formula (I) wherein R is a group

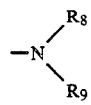

with pharmaceutically acceptable acids, both inorganic acids e.g., hydrochloric, sulfuric or phosphoric acid, and organic acids e.g., citric, fumaric, malic, ascorbic, tartaric, benzoic, acetic, phenylacetic, cyclohexylacetic, 3-cyclohexylpropionic, methanesulfonic, ethanesulfonic, benzenesulfonic, p-toluenesulfonic or p-nitrobenzenesulfonic acid.

Also the quaternary ammonium salts and hydroxides of the compounds of formula (I) wherein R is

are within the scope of the invention: they are, for instance, quaternary alkyl, e.g. methyl, ethyl or cetyl, ammonium salts, e.g. iodides, bromides or chlorides, or hydroxides.

A preferred class of compounds according to the invention are the compounds of formula (I) wherein R is (1) a group —OR'$_4$ wherein R'$_4$ is hydrogen, C$_1$-C$_6$ alkyl or a group —COR'$_5$ wherein R'$_5$ is a C$_1$-C$_{22}$ saturated aliphatic hydrocarbon radical; or (2) a group —SR'$_6$ wherein R'$_6$ has the meanings reported above for R'$_4$;

R$_2$ is hydrogen or fluorine; and either (i) R$_1$ is hydrogen, (a) is single bond and (b) is single or double bond, or (ii) R$_1$ is a group =CHR$_3$ wherein R$_3$ is hydrogen, (a) is double bond and (b) is single bond.

In the above preferred class, when R'$_4$ or R'$_6$ is C$_1$-C$_6$ alkyl, methyl and ethyl are preferred, in particular methyl; when R'$_4$ or R'$_6$ is a group —COR'$_5$, preferably R'$_5$ is C$_1$-C$_{17}$ alkyl, in particular C$_1$-C$_6$ alkyl, especially methyl or ethyl, most preferably methyl.

Examples of specific compounds of the above preferred class are:

1,2β-methylene-4-hydroxyandrost-4-ene-3,17-dione;
1,2β-methylene-4-hydroxy-16α-fluoroandrost-4-ene-3,17-dione;
1,2β-methylene-4-hydroxy-16β-fluoroandrost-4-ene-3,17-dione;
1,2β-methylene-4-hydroxy-6-methylenandrost-4-ene-3,17-dione;
1,2β-methylene-4-hydroxy-6-methylene-16α-fluoroandrost-4-ene-3,17-dione;
1,2β-methylene-4-hydroxy-6-methylene-16β-fluoroandrost-4-ene-3,17-dione;
1,2β-methylene-4-hydroxyandrosta-4,6-diene-3,17-dione;
1,2β-methylene-4-hydroxy-16β-fluoroandrosta-4,6-diene-3,17-dione;
1,2β-methylene-4-hydroxy-16α-fluoroandrosta-4,6-diene-3,17-dione;
1,2β-methylene-4-methoxyandrost-4-ene-3,17-dione;

1,2β-methylene-4-methoxy-16α-fluoroandrost-4-ene-3,17-dione;
1,2β-methylene-4-methoxy-16β-fluoroandrost-4-ene-3,17-dione;
1,2β-methylene-4-methoxy-6-methylenandrost-4-ene-3,17-dione;
1,2β-methylene-4-methoxy-6-methylene-16α-fluoroandrost-4-ene-3,17-dione;
1,2β-methylene-4-methoxy-6-methylene-16β-fluoroandrost-4-ene-3,17-dione;
1,2β-methylene-4-methoxyandrosta-4,6-diene-3,17-dione;
1,2β-methylene-4-methoxy-16β-fluoroandrosta-4,6-diene-3,17-dione;
1,2β-methylene-4-methoxy-16α-fluoroandrosta-4,6-diene-3,17-dione;
1,2β-methylene-4-acetoxyandrost-4-ene-3,17-dione;
1,2β-methylene-4-acetoxy-16α-fluoroandrost-4-ene-3,17-dione;
1,2β-methylene-4-acetoxy-16β-fluoroandrost-4-ene-3,17-dione;
1,2β-methylene-4-acetoxy-6-methylenandrost-4-ene-3,17-dione;
1,2β-methylene-4-acetoxy-6-methylene-16α-fluoroandrost-4-ene-3,17-dione;
1,2β-methylene-4-acetoxy-6-methylene-16β-fluoroandrost-4-ene-3,17-dione;
1,2β-methylene-4-acetoxyandrosta-4,6-diene-3,17-dione;
1,2β-methylene-4-acetoxy-16β-fluoroandrosta-4,6-diene-3,17-dione;
1,2β-methylene-4-acetoxy-16α-fluoroandrosta-4,6-diene-3,17-dione;
1,2β-methylene-4-mercaptoandrost-4-ene-3,17-dione;
1,2β-methylene-4-mercapto-16α-fluoroandrost-4-ene-3,17-dione;
1,2β-methylene-4-mercapto-16β-fluoroandrost-4-ene-3,17-dione;
1,2β-methylene-4-mercapto-6-methylenandrost-4-ene-3,17-dione;
1,2β-methylene-4-mercapto-6-methylene-16α-fluoroandrost-4-ene-3,17-dione;
1,2β-methylene-4-mercapto-6-methylene-16β-fluoroandrost-4-ene-3,17-dione;
1,2β-methylene-4-mercaptoandrosta-4,6-diene-3,17-dione;
1,2β-methylene-4-mercapto-16β-fluoroandrosta-4,6-diene-3,17-dione;
1,2β-methylene-4-mercapto-16α-fluoroandrosta-4,6-diene-3,17-dione;
1,2β-methylene-4-acetylthioandrost-4-ene-3,17-dione;
1,2β-methylene-4-acetylthio-16α-fluoroandrost-4-ene-3,17-dione;
1,2β-methylene-4-acetylthio-16β-fluoroandrost-4-ene-3,17-dione;
1,2β-methylene-4-acetylthio-6-methylenandrost-4-ene-3,17-dione;
1,2β-methylene-4-acetythio-6-methylene-16α-fluoroandrost-4-ene-3,17-dione;
1,2β-methylene-4-acetylthio-6-methylene-16β-fluoroandrost-4-ene-3,17-dione;
1,2β-methylene-4-acetylthioandrosta-4,6-diene-3,17-dione;
1,2β-methylene-4-acetylthio-16β-fluoroandrosta-4,6-diene-3,17-dione;
1,2β-methylene-4-acetylthio-16α-fluoroandrosta-4,6-diene-b 3,17-dione;
1,2β-methylene-4-methyltionandrost-4-ene-3,17-dione;

1,2β-methylene-4-methylthio-16α-fluoroandrost-4-ene-3,17-dione;
1,2β-methylene-4-methylthio-16β-fluoroandrost-4-ene-3,17-dione;
1,2β-methylene-4-methylthio-6-methylenandrost-4-ene-3,17-dione;
1,2β-methylene-4-methylthio-6-methylene-16α-fluoroandrost-4-ene-3,17-dione;
1,2β-methylene-4-methylthio-6-methylene-16β-fluoroandrost-4-ene-3,17-dione;
1,2β-methylene-4-methylthioandrosta-4,6-diene-3,17-dione;
1,2β-methylene-4-methylthio-16β-fluoroandrosta-4,6-diene-3,17-dione;
1,2β-methylene-4-methylthio-16α-fluoroandrosta-4,6-diene-3,17-dione.

Another preferred class of compounds according to the invention are the compounds of formula (I) wherein R is a group

wherein each of $R_8$ and $R_9$, independently, is hydrogen or $C_1$-$C_6$ alkyl;

$R_2$ is hydrogen or fluorine; and either (i) $R_1$ is hydrogen, (a) is single bond and (b) is single or double bond, or (ii) $R_1$ is a group $=CHR_3$ wherein $R_3$ is hydrogen, (a) is double bond and (b) is single bond.

and the pharmaceutically acceptable salts thereof.

In the above preferred class a $C_1$-$C_6$ aklyl group for $R_8$ and/or $R_9$ is, preferably, methyl of ethyl.

Preferred groups

are amino, methylamino, ethylamino, dimethylamino and diethylamino, most preferably amino.

Examples of specific compounds of the above preferred class are:
1,2β-methylen-4-aminoandrost-4-ene-3,17-dione;
1,2β-methylen-4-amino-16α-fluoroandrost-4-ene-3,17-dione;
1,2β-methylen-4-amino-16β-fluoroandrost-4-ene-3,17-dione;
1,2β-methylen-4-amino-6-methylenandrost-4-ene-3,17-dione;
1,2β-methylen-4-amino-6-methylene-16α-fluoroandrost-4-ene-3,17-dione;
1,2β-methylen-4-amino-6-methylene-16β-fluoroandrost-4-ene-3,17-dione;
1,2β-methylen-4-aminoandrosta-4,6-diene-3,17-dione;
1,2β-methylen-4-amino-16β-fluoroandrosta-4,6-diene-3,17-dione;
1,2β-methylen-4-amino-16α-fluoroandrosta-4,6-diene-3,17-dione, and the pharmaceutically acceptable salts thereof.

The compounds of the invention may be prepared by a process comprising:

(A) treating a compound of formula (II)

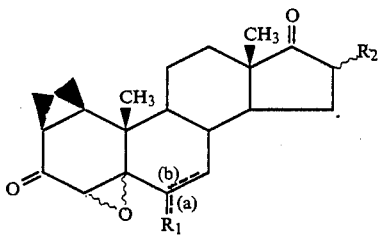
(II)

wherein $R_1$, $R_2$, (a), (b) and the symbol ⚌ are defined above, or solvolysis so as to obtain a compound of formula (I) wherein R is a group —$OR_4$ wherein $R_4$ is, respectively, hydrogen, $C_1$-$C_6$ alkyl, or a phenyl or benzyl group unsubstituted or ring-substituted as reported above; or (B) etherifying a compound of formula (I) wherein R is OH, so as to obtain a compound of formula (I) wherein R is a group —$OR_4$ wherein $R_4$ is $C_1$-$C_6$ alkyl or, respectively, a hydroxy protecting group; or (C) reacting a compound of formula (II) with a compound of formula (III)

$R'_6$—SH  (III)

wherein $R'_6$ is hydrogen, $C_1$-$C_6$ alkyl or a phenyl or benzyl group, each unsubstituted or ring-substituted as indicated above, so obtaining a compound of formula (I) wherein R is a group —$SR_6$, wherein $R_6$, according to the reaction conditions, either has the meanings reported above for $R'_6$ or is a group —$SR_7$ wherein $R_7$ is a steroidic residue as defined above under (vi) in which $R_1$, $R_2$, (a), (b) and the symbol ⚌ are the same as in the starting compound of formula (II); or (D) acylating a compound of formula (I) wherein R is —OH or, respectively, —SH, with a reagent carrying a —$COR_5$ moiety, wherein $R_5$ is as defined above, so obtaining a compound of formula (I) wherein R is a group —$OR_4$ or, respectively, a group —$SR_6$ wherein $R_4$ and, respectively, $R_6$ are a group —$COR_5$ wherein $R_5$ is a defined above; or (E) reacting a compound of formula (I) wherein R is —SH with a compound of formula (IV)

$R_7$—SH  (IV)

wherein $R_7$ is as defined above, so obtaining a compound of formula (I) wherein R is —$SR_6$ wherein $R_6$ is a group —$SR_7$ in which $R_7$ is as defined above; or (F) reacting a compound of formula (II) with a compound of formula (V)

M—$N_3$  (V)

wherein M is an alkali metal or ammonium cation or a tri—$C_1$-$C_6$—alkylsilyl group, so obtaining a compound of formula (I) wherein R is the group —$N_3$; or (G) reducing a compound of formula (I) wherein R is the group —$N_3$, so obtaining a compound of formula (I) wherein R is a group

wherein $R_8$ and $R_9$ are both hydrogen; or (H) alkylating a compound of formula (I) wherein R is a group

wherein $R_8$ and $R_9$ are both hydrogen, so obtaining a compound of formula (I) wherein R is a group

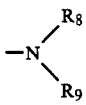

wherein at least one of $R_8$ and $R_9$ is $C_1$-$C_6$ alkyl;

and, if desired, salifying a compound of formula (I) containing a salifiable group or obtaining a free compound from a salt and/or, if desired, separating a mixture of isomers of formula (I) into the single isomers.

The solvolysis of a compound of formula (II) in order to obtain a compound of formula (I) wherein R is a group —$OR_4$ wherein $R_4$ is hydrogen may be carried out, e.g., by treatment with suitable mineral acids e.g., sulfuric acid, hydrochloric acid, phosphoric acid, acetic acid, or a mixture thereof, at a temperature ranging from about the room temperature to about the reflux temperature. Preferably the reaction is carried out by treatment with a mixture of glacial acetic acid and concentrated sulfuric acid, at a temperature ranging from about 10° C. to about 50° C., e.g., according to B. Camerino et al., 1956, Il Farmaco 7, 19.

Alternatively the solvolysis may be carried out in an alkaline aqueous solvent at a temperature between the room temperature and the reflux temperature.

Preferably the reaction is carried out in a tertiary alcohol, e.g. in tert. butyl alcoholic solution by treatment with 40% aqueous tetrabutylammonium hydoxide at a temperature ranging from the room temperature to reflux.

The solvolysis of a compound of formula (II) in order to obtain a compound of a formula (I) wherein R is a group —$OR_4$ wherein $R_4$ is $C_1$-$C_6$ alkyl, may be, e.g, carried out by treatment with a suitable $C_1$-$C_6$ alkyl-alcohol in aqueous solution, in the presence of an alkali which is, preferably, an alkali metal, e.g., sodium or potassium, hydroxide, at a temperature ranging, e.g., from about 20° C. to the reflux temperature, for reaction times varying, e.g., from about 1 hour to about 48 hours, for instance according to B. Camerino et al., 1962, Gazz. Chim, It. 92,709. In similar way, solvolysing the compound (II) with the appropriate phenol derivative or benzyl alcohol derivative, a compound (I) wherein R is a group —$OR_4$ in which $R_4$ is a phenyl or benzyl group either unsubstituted or ring-substituted as indicated above, may be obtained.

The etherification of a compound of formula (I) wherein R is —OH to give a compound of formula (I) wherein R is a group —$OR_4$ wherein $R_4$ is $C_1$-$C_6$ alkyl or a hydroxy protecting group, may be carried out by the usual procedures described in the organic chemistry for converting alcohols into ethers; for instance $C_1$-$C_6$ alkyl ethers may be obtained by reaction with the appropriate diazoalkane or $C_1$-$C_6$ alkyl halide under standard conditions, and, e.g., silyl ethers may be prepared by reaction with the appropriate silyl halide in the presence of a base, again using conventional procedures. The reaction between a compound of formula (II) and a compound of formula (III) wherein $R_6'$ is hydrogen (i.e. hydrogen sulfide) leading, by oxirane ring cleavage, to a compound of formula (I) wherein R is a group —$SR_6$ wherein $R_6$ is hydrogen may be carried out in presence of a base, either organic such as, for instance, pyridine or a tri-$C_1$-$C_6$-alkylamine, e.g. triethylamine, or inorganic such as, e.g., NaOH or KOH, operating in an inert solvent, such as, for example, methanol, ethanol, water, dioxane or dimethoxyethane, and under inert atmosphere.

When the reaction is carried out under air or oxygen atmosphere, the dimeric disulfide is obtained, i.e. the compound of formula (I) wherein R is —$SR_6$ with $R_6$ being a group —$SR_7$ in which $R_7$ is a steroidic residue as defined above under (vi) having for $R_1$, $R_2$, (a), (b) and the symbol ⁝⁝⁝ the same meanings as the starting compound of formula (II). The reaction between a compound of formula (II) and a compound of formula (III) wherein $R'_6$ is $C_1$-$C_6$ alkyl or a phenyl or benzyl group as defined above, leading, by oxirane ring cleavage, to a compound of formula (I) wherein R is a group —$SR_6$ wherein $R_6$ is $C_1$-$C_6$ alkyl or a phenyl or benzyl group as defined above, may be carried out in presence of an acid such as, for example, polyphosphoric acid, operating in an inert solvent which may be, for instance, dioxane, dimethoxyethane, water, methanol or ethanol at a temperature between about 0° C. and about 50° C.

The acylation of a compound of formula (I) wherein R is —OH or, respectively, —SH, in order to obtain a compound of formula (I) wherein R is a group —$OR_4$ or, respectively, a group —$SR_6$ wherein $R_4$ and, respectively, $R_6$ are a group —$COR_5$ wherein $R_5$ is a defined above, may be performed by reaction with a suitable acylating agent carrying the —$COR_5$ moiety, which may be, for example, a reactive derivative of the appropriate carboxylic acid, e.g., a halide, preferably the chloride or the anhydride or a mixed anhydride, thereof, in the presence of a basic agent, preferably an organic base, e.g., pyridine.

The reaction between a compound of formula (I), wherein R is —SH and a compound of formula (IV), in order to obtain a compound of formula (I) wherein R is a group —$SR_6$ wherein $R_6$ is —$SR_7$ with $R_7$ as defined above, may be performed according to known methods for the formation of disulfides, e.g. as described in Comprehensive Organic Chemistry, Vol. 3, pag. 283-6, Pergamon Press.

When M in the compound (V) is an alkali metal, this is, preferably, sodium, potassium or lithium; when M is a tri-$C_1$-$C_6$ alkyl silyl group, this is preferably, trimethylsilyl or dimethyl-tert-butylsilyl.

Preferred compounds (V) are sodium azide, lithium azide, trimethylsilyl azide and dimethyl tert-butyl silyl azide. The reaction between a compound of formula (II) and a compound of formula (V) is preferably carried out in a dipolar aprotic solvent such as, N,N-dimethylformamide or dimethylsulfoxide; some water or an aqueous alcoholic, e.g. methanolic or ethanolic, solution may be added, if desired, to increase the solubility of the azide (V). The reaction temperature e.g., from about 0° C. to about 60° C. Some acid, e.g. sulfuric acid may be added, if desired, to increase the reactivity of the oxirane ring.

The reduction of a compound of formula (I) wherein R is the group —$N_3$ in order to obtain a compound of formula (I) wherein R is a group

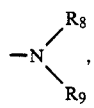

wherein $R_8$ and $R_9$ are both hydrogen, may be carried out following known methods, for instance, with a variety of reducing agents, e.g. propane-1,3-dithiol in triethylamine, as described in Tetr. Lett., 39, 3633 (1978); dithiolthreitol in aqueous solutions; mercaptoacetic acid and triethylamine; or, for instance, triphenylphosphine in tetrahydrofuran and aqueous solution, as described, e.g., in Bull. Soc. Chim. Fr., 1985, 815.

The alkylation of a compound of formula (I) wherein R is a group

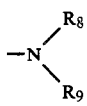

wherein $R_8$ and $R_9$ are both hydrogen to obtain a corresponding compound of formula (I) wherein R is a group

wherein at least one of $R_8$ and $R_9$ is $C_1$-$C_6$ alkyl, may be carried out by reaction with a suitable alkylating agent, which may be, e.g., a $C_1$-$C_6$ alkyl halide, in particular iodide, or di —$C_1$-$C_6$—alkyl sulfate; for obtaining a compound of formula (I) wherein R is a group

wherein at least one of $R_8$ and $R_9$ is methyl or ethyl, suitable alkylating agents are, e.g., methyl iodide, dimethylsulfate or, respectively, ethyliodide and diethylsulfate. Reaction conditions well known to the skilled in the art and well described in the organic chemistry may be followed: see, e.g., Lucier et al., Org. Synth. 44, 72 (1964).

A compound of formula (II) wherein $R_1$, $R_2$, (a), (b) and the symbol ⁝⁝⁝ are as defined above may be prepared by epoxidation ofc a compound of formula (VI)

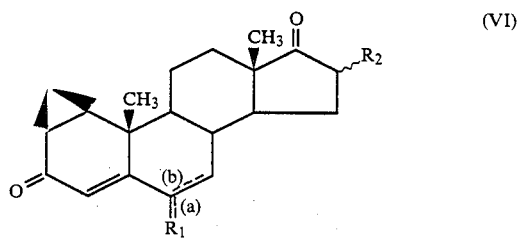

wherein, $R_1$, $R_2$, (a), (b) and the symbol ⁝⁝⁝ are as defined above. The epoxidation may be carried out by treatment with a suitable oxidizing agent which may be, for instance, concentrated, e.g. 36%, hydrogen peroxide in alcoholic alkali-metal hydroxide solution, preferably KOH or NaOH in methanol, at a temperature ranging e.g., approximately, from 0° C. to 25° C. for a time of from about 2 hrs to several days.

The compounds of formula (VI) wherein $R_1$ is hydrogen, (a) is single bond, (b) is single or double bond and $R_2$ is hydrogen are known compounds described, e.g., in the published German patent application No. 3, 422, 187.

A compound of formula (VI) wherein $R_1$ is hydrogen, (a) is single bond, (b) is single or double bond and $R_2$ is fluorine may be prepared from the corresponding compouns of formula (VI) wherein $R_2$ is hydrogen by known methods, for instance by the process described by J. A. Katzenellenbogen et al., in J. Org. Chem., 49, 4900 (1984).

A compound of formula (VI) wherein $R_1$ is a group $=CHR_3$ as defined above, (a) is double bond and (b) is single bond may be obtained by alkylidenation of the corresponding compound wherein $R_1$ is hydrogen and (a) and (b) are both single bonds according to known methods e.g. the method of K. Annen, Synthesis 1982, 34. Preferably the reaction is carried out, e.g., with an unsubstituted or appropriately $C_1$-$C_6$ alkyl substituted formaldehyde diethylacetal in refluxing chloroform in the presence of phosphoryl chloride and sodium acetate. Alternatively, the same reaction may be carried out in other inert solvents, e.g. 1,2-dichloroethane, diethyl ether or dioxane, and in the presence of other suitable condensing agents, e.g. phosphorous pentoxide or p-toluene sulfonic acid.

The compounds having the formulae (III), (IV) and (V) are known compounds or may be prepared by known methods from known compounds.

The compounds of the present invention are inhibitors of the biotransformation of androgens into estrogens, i.e., they are steroidal aromatase inhibitors.

The aromatase inhibitory activity of these compounds is shown, e.g., by the fact that they are active in the in vitro test described by Thompson and Siiteri (E. A. Thompson and P. K. Siiteri, J. Biol. Chem. 249, 5364, 1974) which utilizes the human placental microsomal fraction as enzyme source. In this test the aromatization rate of androstenedione into estrone was evaluated by incubating [$1\beta,2\beta$-$^3$H]androstenedione (50 nM) in the presence of NADPH with the enzyme preparation and by measuring the amount of $^3H_2O$ formed during 20 min incubation at 37° C.

By virtue of their ability to inhibit aromatase and, consequently, to reduce estrogen levels, the new compounds of the invention may be useful in the treatment and prevention of various estrogen dependent diseases, e.g., breast, endometrial, ovarian and pancreatic cancers, gynecomastia, benign breast disease, endometriosis, polycystic ovarian disease and precocious puberty. Another application of the compounds of the invention may be in the therapeutic and/or prophylactic treatment of prostatic hyperplasia, a disease of the estrogen dependent stromal tissue. The new compounds can find also use for the treatment of male infertility associated with oligospermia and for female fertility control, by virtue of their ability to inhibit ovulation and egg nidation.

In view of their high therapeutic index, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar of film coated tablets, liquid solutions or suspensions; rectally, in the form of suppositories; parenterally, e.g. intramuscularly, or by intravenous injection of infusion; or topically.

The dosage depends on the age, weight, conditions of the patient and administration route; for example the dosage adopted for oral administration to adult humans may range from about 10 to about 150–200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate; and/or polyethylene glycols; binding agents, e.g. starches, arabic gums, gelatin, methylcellulose, carboxymethylcellulose or polyvinil pyrrolidone; disaggregating agents, e.g. a starch, alginic acid, alginates or sodium starch glycolate; effervescing mixtures; dyestuff; sweeteners; wetting agents, such as lecithin, polysorbates, laurysulphates; and, in general, nontoxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersion for oral administration may be e.g. syrups, emulsions and suspensions.

The syrup may contain as carrier, for example, saccharose or saccharose with glycerine and/or mannitol and/or sorbitol.

The suspensins and the emulsions may contain as carrier, for example, a natural gun, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusione may contain as carrier, for example, sterile water or, preferably, they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin. Compositions for topical appliation e.g., creams, lotions or pastes, e.g., prepared by admixing the active ingredient, with a conventional oleaginous or emulsifying excipient.

The following examples illustrate but do not limit the invention.

EXAMPLE 1

1,2β-methylen-4,5-epoxyandrostane-3,17-dione [II, R₁=R₂=H; (a) and (b)=single bonds]

1,2β-methylenandrost-4-ene-3,17-dione (2.984 g, 10 mmol) is dissolvd in 120 ml of methanol and cooled to 0° C. Thereupon ice cold 36% H₂O₂ (10 ml) and 2% NaOH (5 ml) is added.

The mixture is stirred for 1 hour, allowed to stand at 5° C. for 20 hours and then poured into 900 ml of ice water with vigorous stirring. The raw product is filtered off, washed with water, dried in the oven and finally chromatographed on silica gel using CHCl₃ as eluant to give 2.515 g (80%) of pure title compound.

Elemental analysis calculated % (found %): C 76.40 (76.36), H 8.34 (8.29).

NMR (CHCl₃, δ): 0.91 (3H, s), 1.38 (3H, s) 3.03 (1H, br s)

In analogous fashion the following compounds can be prepared:

1,2β-methylen-4,5-epoxy-16α-fluoroandrostane-3,17-dione; and 1,2β-methylen-4,5-epoxy-16β-fluoroandrostane-3,17-dione.

EXAMPLE 2

1,2β-methylen-4,5-epoxyandrost-6-ene-3,17-dione [II, R₁=R₂=H; (a)=single bond; (b)=double bond].

To a cooled solution of 1,2β-methylenandrosta-4,6-diene-3,17-dione (2.964 g, 10 mmol) in 120 ml methanol ice cold 36% H₂O₂ (10 ml) and 2% NaOH (5 ml) is added gradually under stirring and then the mixture allowed to stand at 0°–5° C. for about 20 hours. Then the reaction mixture is poured onto ice, the raw product filtered off, washed with water, dried and purified by column chromatography on silica gel, using CHCl₃ as eluant. Thus 2.655 g (85%) of pure title compound is obtained.

Elemental analysis calculated % (found %): C 76.89 (76.65), H 7.74 (7.69)

In analogous fashion the following compounds can be prepared:

1,2β-methylen-4,5-epoxy-16α-fluoroandrost-6-ene-3,17-dione; and 1,2β-methylen-4,5-epoxy-16β-fluoroandrost-6-ene-3,17-dione.

EXAMPLE 3

1,2β-methylene-6-methylenandrost-4-ene-3,17-dione [VI, R₁=CH₂; R₂=H; (a)=double bond; (b)=single bond].

A mixture of sodium acetate (1 g), absolute chloroform (30 ml), formaldehyde diethyl acetal (30 ml, 0.24 mol), phosphoryl chloride (3.8 ml, 40 mmol), and 1,2β-methylenandrost-4-ene-3,17-dione (0.806 g, 2.7 mmol) is stirred at reflux for about 7 hours, i.e. until the starting material has disappeared. The suspension is allowed to cool and under vigorous stirring a saturated sodium carbonate solution is added dropwise until the pH of the aqueous layer becomes alkaline (about 1 hour). The organic layer is separated, neutralized with water, and dried with sodium sulfate. After concentration under reduced pressure the oily residue is purified by column chromatography on silica gel using n-hexane/ethylacetate as eluant. The pure title compound is obtained in 60% yield (0.503 g).

Elemental analysis calculated % (found %): C 81.25 (81.10), H 8.44 (8.35)

NMR (CHCl₃, δ): 0.92 (3H, s), 1.18 (3H, s), 4.82 (2H, m) 5.60 (1H, s)

In analogous fashion the following compounds can be prepared:

1,2β-methylene-6-methylene-16α-fluoroandrost-4-ene-3,17-dione; and 1,2β-methylene-6-methylene-16β-fluoroandrost-4-ene-3,17-dione.

EXAMPLE 4

1,2β-methylen-4,5-epoxy-6-methylenandrostane-3,17-dione [II, R₁=CH₂; R₂=H; (a)=double bond, (b)=single bond].

1,2β-methylen-6-methylenandrost-4-ene-3,17-dione (3.104 g, 10 mmol) is dissolved in 120 ml of methanol and cooled to 0° C. Thereupon ice cold 36% H₂O₂ (10 ml) and 2% NaOH (5 ml) is added gradually, the reaction mixture kept for about 20 hours at 5° C. and then poured into 900 ml of ice water. The raw product is filtered off, washed with water, dried and then chromatographed on silica gel using CHCl₃ as eluant. Thus pure title compound is obtained in 60% yield (1.959 g).

Elemental analysis calculated % (found %): C 77.27 (77.15), H 8.03 (7.95).

In analogous fashion the following compounds can be prepared:

1,2β-methylen-4,5-epoxy-6-methylene-16α-fluoroandrostane-3,17-dione; and 1,2β-methylen-4,5-epoxy-6-methylene-16β-fluoroandrostane-3,17-dione.

EXAMPLE 5

1,2β-methylene-4-hydroxyandrost-4-ene-3,17-dione [I, R=OH; R₁=R₂=H; (a) and (b)=single bonds].

A mixture of 1,2β-methylen-4,5-epxoyandrostane-3,17-dione (0.314 g, 1 mmol), 40% tetrabutyl-ammonium hydroxide (8 ml) and tert-butyl alcohol (36 ml) is stirred at 100° C. under nitrogen for 3 hours. To the cooled mixture water is added, the raw product extracted with CHCl₃, the organic layer dried and evaporated. The resulting residue is chromatographed on silica gel using benzene/diethylether 3% as eluant to give pure title compound in 60% yield (0.188 g).

Elemental analysis calculated % (found %): C 76.40 (76.35), H 8.34 (8.25).

NMR (CHDl₃, δ): 0.80 (2H, m), 0.93 (3H, s), 1.28 (3H, s), 2.92 (1H, m), 6.08 (1H, br s).

In analogous fashion the following compounds can be prepared:

1,2β-methylene-4-hydroxy-16α-fluoroandrost-4-ene-3,17-dione;

1,2β-methylene-4-hydoxy-16β-fluoroandrost-4-ene-3,17-dione;

1,2β-methylene-4-hydroxy-6-methylenandrost-4-ene-3,17-dione;

1,2β-methylene-4-hydroxy-6-methylene-16α-fluoroandrost-4-ene-3,17-dione;

1,2β-methylene-4-hydroxy-6-methylene-16β-fluoroandrost-4-ene-3,17-dione;

1,2β-methylene-4-hydroxy-androsta-4,6-diene-3,17-dione;

1,2β-methylene-4-hydroxy-16α-fluoroandrosta-4,6-diene-3,17-dione;

1,2β-methylene-4-hydroxy-16β-fluoroandrosta-4,6-diene-3,17-dione.

EXAMPLE 6

1,2β-methylene-4-methoxyandrost-4-ene-3,17-dione [I, R=—OMe; $R_1=R_2=H$, (a) and (b)=single bonds].

To a stirred solution of 1,2β-methylen-4,5-epoxyandrostane-3,17-dione (0.653 g, 2 mmole) in methanol (63 ml) 4N aqueous sodium hydroxide (6.3 ml) is added. The resulting mixture is refluxed for 1 hr, cooled to room temperature, evaporated in vacuo, taken up with water, neutralized with 37% hydrochloric acid and kept at 0°–5° C. overnight. The resulting precipitate is filtered off, washed with water, dried and purified by flash column chromatography on silica gel eluting with n-hexane:ethyl acetate 60:40. There are obtained 0.511 g (75% yield) of the title compound.

Elemental analysis calculated % (found %): C 76.79 (76.65), H 8.59 (8.49).

NMR (CHCl$_3$, δ): 0.80 (2H, m), 0.90 (3H, s), 1.29 (3H, s), 2.93 (1H, m), 3.55 (3H, s).

In analogous fashion the following compounds can be prepared:

1,2β-methylene-4-methoxy-16α-fluoroandrost-4-ene-3,17-dione;

1,2β-methylene-4-methoxy-16β-fluoroandrost-4-ene-3,17-dione;

1,2β-methylene-4-methoxy-6-methylenandrost-4-ene-3,17-dione;

1,2β-methylene-4-methoxy-6-methylene-16α-fluoroandrost-4-ene-3,17-dione;

1,2β-methylene-4-methoxy-6-methylene-16β-fluoroandrost-4-ene-3,17-dione;

1,2β-methylene-4-methoxy-androsta-4,6-diene-3,17-dione;

1,2β-methylene-4-methoxy-16α-fluoroandrosta-4,6-diene-3,17-dione;

1,2β-methylene-4-methoxy-16β-fluoroandrosta-4,6-diene-3,17-dione.

EXAMPLE 7

1,2β-methylene-4-mercaptoandrost-4-ene-3,17-dione [I, R=—SH, $R_1=R_2=H$, (a) and (b)=single bonds]

To a stirred solution of 1,2β-methylen-4,5-epoxyandrostane-3,17-dione (0.408 g, 1.25 mmole) in dioxane (12 ml) and ethanol (12 ml) is added dropwise a solution of technical sodium hydrosulfide (0.55 g) in ethanol (25 ml) at 10° C. under nitrogen. The resulting reaction mixture is stirred at room temperature for 1 hour, neutralized with glacial acetic acid (1 ml) and extracted with chloroform (50 ml). The organic extract is washed with water, saturated NaHCO$_3$ solution, water, and then driedover sodium sulfate. The solvent is evaporated in vacuo and the crude product is column chromatographed over silica gel eluting with benzene. There are obtained 0.227 g (55%) of the title compound.

Elemenal analysis calculated % (found %): C 72.72 (72.55) H 7.87 (7.65) S 9.69 (9.53)

I.R. (KBr, cm$^{-1}$): 2560, 1730, 1660, 1560. In analogous fashion the following compounds can be prepared:

1,2β-methylene-4-mercapto-16α-fluoroandrost-4-ene-3,17-dione;

1,2β-methylene-4-mercapto-16β-fluoroandrost-4-ene-3,17-dione;

1,2β-methylene-4-mercapto-6-methylenandrost-4-ene-3,17-dione;

1,2β-methylene-4-mercapto-6-methylene-16α-fluoroandrost-4-ene-3,17-dione;

1,2β-methylene-4-mercapto-6-methylene-16β-fluoroandrost-4-ene-3,17-dione;

1,2β-methylene-4-mercapto-androsta-4,6-diene-3,17-dione;

1,2β-methylene-4-mercapto-16α-fluoroandrosta-4,6-diene-3,17-dione;

1,2-β-methylene-4-mercapto-16β-fluoroandrosta-4,6-diene-3,17-dione.

EXAMPLE 8

1,2β-methylene-4-methylthioandrost-4-ene 3,17-dione [I, R=—SMe; $R_1=R_2=H$; (a) and (b) single bonds]

Into a stirred solution of 1,2β-methylen-4,6-epoxyandrostane-3,17-dione (0.78 g, 2.47 mmole) and polyphosphoric acid (1.5 g) in dioxane (30 ml) methylthiol is bubbled at room temperature under nitrogen. The reaction mixture is stirred for 6 hours and allowed to stand for a further 40 hours, then it is poured into a mixture of water and crushed ice, neutralized with sodium bicarbonate (3 g) and extracted with ethyl acetate. The combined extracts are washed with brine and dried over sodium sulfate. The solution is evaporated in vacuo and the resulting residue is column chromatographed over silica gel.

Elution with benzene affords 3,4-bis (methylthio)-1,2β-methylenandrost-3-en-17-one (0.410 g). Further elution with benzene:ethyl acetate 90:10 affords the title product. The former product dissolved in chloroform (30 ml) is treated with gaseous HCl during 3 hours with cooling to give, after evaporation of the solvent, more title product (0.20 g). The two aliquots are combined and crystallized from methanol to yield the title compound (0.350 g, 40% yield).

Elemental analysis calculated % (found %): C 73.21 (73.15), H 8.19 (8.10), S 9.31 (9.22)

I.R. (KBr, cm$^{-1}$): 1740, 1680, 1555 In analogous fashion the following compounds can be prepared:

1,2β-methylene-4-methylthio-16α-fluoroandrost-4-ene-3,17-dione;

1,2β-methylene-4-methylthio-16β-fluoroandrost-4-ene-3,17-dione;

1,2β-methylene-4-methylthio-6-methylenandrost-4-ene-3,17-dione;

1,2β-methylene-4-methylthio-6-methylene-16α-fluoroandrost-4-ene-3,17-dione;

1,2β-methylene-4-methylthio-6-methylene-16β-fluoroandrost-4-ene-3,17-dione;

1,2β-methylene-4-methylthio-androst-4,6-diene-3,17-dione;

1,2β-methylene-16α-fluoroandrosta-4,6-diene-3,17-dione;

1,2β-methylene-4-methylthio-16β-fluoroandrosta-4,6-diene-3,17-dione.

EXAMPLE 9

1,2β-methylen-4-aminoandrosta-4,6-diene-3,17-dione [I, R=—NH$_2$; $R_1=R_2=H$, (a)=single bond, (b)=double bond]

To a stirred solution of 1,2β-methylen-4,5-epoxyandrostane-3,17-dione (0.41 g, 1.305 mmole) in dry dimethylsulfoxide (6.5 ml) is added conc. sulfuric acid (0.1 ml) and sodium azide (1.36 g). The resulting reaction mixture is treated at about 110° C. during 3 hours, cooled, poured into a mixture of water (50 ml) and conc. hydrochloric acid (4 ml), and extracted with ethyl acetate (3×50 ml). The combined organic extracts are dried over sodium sulfate, filtered and evaporated in vacuo to yield a solid which is purified by flash column chromatography eluting with n-hexane:diethyl ether 6:4. There are obtained 0.244 g (60% yield) of the title compound.

Elemental analysis calculated % (found %): C 77.13 (77.05), H 8.09 (8.01), N 4.50 (4.39) In analogous fashion the following compounds can be prepared:

1,2β-methylen-4-amino-16α-fluoroandrosta-4,6-diene-3,17-dione; and 1,2β-methylen-4-amino-16β-fluoroandrosta-4,6-diene-3,17-dione.

EXAMPLE 10

1,2β-methylen-4-aminoandrost-4-ene-3,17-dione [I, R=—$NH_2$; $R_1=R_2=H$; (a) and (b)=single bonds]

To a stirred solution of 1,2β-methylen-4,5-epoxyandrostane-3,17-dione (0.50 g, 1.59 mmole) in dry dimethylsulfoxide (7.5 ml) is added conc. sulfuric acid (0.11 ml) and sodium azide (1.4 g). The resulting reaction mixture is heated at about 85° C. during 3 hours, cooled, poured into a mixture of water (50 ml) and conc. hydrochloric acid (4 ml), and extracted with ethyl acetate (3×50 ml). The combined organic extracts are dried over sodium sulfate, filtered and evaporated in vacuo to yield a solid which is purified by flash column chromatography eluting with n-hexane-diethyl ether 6:4. There are obtained 0.378 g (70% yield) of 1,2β-methylen-4-azidoandrost-4-ene-3,17-dione [I, R=—N, $R_1=R_2=H$; (a) and (b)=single bonds]

elemental analysis calculated % (found %): C 70.77 (70.55), H 7.42 (7.31)

NMR (CHCl$_3$, δ): 0.7–1.0 (2H, m), 0.91 (3H, s), 1.29 (3H, s), 2.90 (1H, m).

This 4-azido-derivative is dissolved in tetrahydrofuran (4 ml) and treated by the portionwise addition of triphenyl phosphine (0.4 g) at room temperatures, followed by the addition of water (1 ml). The resulting reaction mixture is heated at reflux for 24 hours, cooled, diluted with 50 ml of 1N HCl and washed with methylene chloride (2×50 ml) which is discarded. The aqueous phase is adjusted to pH 10 and extracted with methylene chloride (3×50 ml). The combined organic extracts are washed with water, dried over sodium sulfate and evaporated in vacuo. The resulting residue is purified by flash column chromatography eluting with n-hexane-diethylether. There are obtained 0.227 g (65% yield) of 1,2β-methylen-4-aminoandrost-4-ene-3,17-dione.

Elemental analysis calculated % (found %): C 76.64 (76.45), H 8.68 (8.55), N, 4.47 (4.38)

NMR (CHCl$_3$, δ): 0.75 (2H, m), 0.92 (3H, s), 3.0 (2H, br).

In analogous fashion the following compounds can be prepared:

1,2β-methylen-4-amino-16α-fluoroandrost-4-ene-3,17-dione;

1,2β-methylen-4-amino-16β-fluoroandrost-4-ene-3,17-dione;

1,2β-methylen-4-amino-6-methylenandrost-4-ene-3,17-dione;

1,2β-methylen-4-amino-6-methylene-16α-fluoroandrost-4-ene-3,17-dione; and 1,2β-methylen-4-amino-6-methylene-16β-fluoroandrost-4-ene-3,17-dione.

EXAMPLE 11

1,2β-methylen-4-acetoxyandrost-4-ene-3,17-dione [I, R=—OCOCH$_3$; $R_1=R_2=H$; (a) and (b)=single bonds]

To a cooled solution of 1,2β-methylene-4-hydroxyandrost-4-ene-3,17-dione (0.40 g, 1.27 mmole) in dry pyridine (3 ml) is added acetic anhydride (1 ml). The mixture is kept at 0°–5° C. overnight, then it is poured into cold water. The resulting precipitate is filtered off, thoroughly washed with water, dried in vacuo and crystallized from methanol:acetone 50:40. There are obtained 0.35 g (77% yield) of the title compound.

Elemental analysis calculated % (found %): C 74.13 (74.05), H 7.92 (7.85).

In analogous fashion the following compounds can be prepared:

1,2β-methylen-4-acetoxy-16α-fluoroandrost-4-ene-3,17-dione;

1,2β-methylen-4-acetoxy-16β-fluoroandrost-4-ene-3,17-dione;

1,2β-methylen-4-acetoxy-6-methylenandrost-4-ene-3,17-dione;

1,2β-methylen-4-acetoxy-6-methylene-16α-fluoroandrost-4-ene-3,17-dione;

1,2β-methylen-4-acetoxy-6-methylene-16β-fluoroandrost-4-ene -3,17-dione;

1,2β-methylen-4-acetoxyandrosta-4,6-diene-3,17-dione;

1,2-methylen-4-acetoxy-16α-fluoroandrosta-4,6-diene-3,17-dione;

1,2β-methylen-4-acetoxy-16β-fluoroandrosta-4,6-diene-3,17-dione;

1,2β-methylen-4-acetylthioandrost-4-ene-3,17-dione;

1,2β-methylen-4-acetylthio-16α-fluoroandrost-4-ene-3,17-dione;

1,2β-methylen-4-acetylthio-16β-fluoroandrost-4-ene-3,17-dione;

1,2β-methylen-4-acetylthio-6-methylenandrost-4-ene-3,17-dione;

1,2β-methylen-4-acetylthio-6-methylene-16α-fluoroandrost-4-ene-3,17-dione;

1,2β-methylen-4-acetylthio-6-methylene-16β-fluoroandrost-4-ene-3,17-dione;

1,2β-methylen-4-acetylthioandrosta-4,6-diene-3,17-dione;

1,2β-methylen-4-acetylthio-16α-fluoroandrosta-4,6-diene-3,17-dione; and 1,2β-methylen-4-acetylthio-16β-fluoroandrosta-4,6-diene-3,17-dione.

EXAMPLE 12

1,2β-methylene-4-methoxyandrost-4-ene-3,17-dione [I, R=OMe; $R_1=R_2=H$; (a) and (b)=single bonds]

To a solution of 1,2β-methylene-4-hydroxyandrost-4-ene-3,17-dione (0.314 g, 1 mmol) in benzene (10 ml) potassium tert-butoxide (0.224 g, 2 mmol) is added and the mixture heated to reflux for 30 min. After cooling, iodomethane (0.710 g, 5 mmol) is added and the mixture boiled for further 2 hours. Then the organic solution is washed with water, dried and evaporated in vacuum. The flash column chromatography of the residue on silica gel using n-hexane/ethylacetate 60:40 affords 0.246 g (75% yield) of the title compound.

Elemental analysis calculated % (found %): C 76.79 (76.63), H 8.59 (8.40).

NMR (CHCl$_3$, δ): 0.80 (2H, m), 0.90 (3H, s), 1.29 (3H, s), 2.93 (1H, m), 3.55 (3H, s).

Following the above described procedure and starting from the appropriate 4-hydroxyderivative the compounds mentioned in example 6 can be prepared.

EXAMPLE 13

Tablets each weighing 0.150 g and containing 25 mg of the active substance, can be manufactured as follows:

| Composition (for 10,000 tablets) | |
|---|---|
| 1,2β-methylene-4-hydroxyandrost-4-ene-3,17-dione | 250 g |
| Lactose | 800 g |
| Corn starch | 415 g |
| Talc powder | 30 g |
| Magnesium stearate | 5 g |

The 1,2β-methylene-4hydroxyandrost-4-ene-3,17-dione, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 14

Capsules, each dosed at 0.200 g and containing 20 mg of the active substance can be prepared with the following composition for 500 capsules:

| 1,2β-methylene-4-hydroxyandrost-4-ene-3,17-dione | 10 g |
|---|---|
| Lactose | 80 g |
| Corn starch | 5 g |
| Magnesium stearate | 5 g |

This formulation can be encapsulated in two-piece hard gelatin capsules and dosed at 0.200 g for each capsule.

We claim:

1. A compound of formula (I)

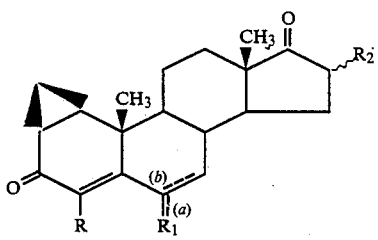

wherein $R_1$ is hydrogen or a group $=CHR_3$ wherein $R_3$ is hydrogen or $C_1-C_6$ alkyl; the symbol  indicates the presence of a single or double bond in such a way that, when $R_1$ is hydrogen, (a) is single bond and (b) is either single or double bond, while, when $R_1$ is a group $=CHR_3$ as defined above, (a) is double bond and (b) is single bond; $R_2$ is hydrogen or fluorine; and R is
  (1) a group $—OR_4$ wherein $R_4$ is
    (a) hydrogen;
    (b) $C_1-C_6$ alkyl;
    (c) a phenyl or benzyl group, each unsubstituted or ring-substituted by one or more substituents chosen from $C_1-C_4$ alkyl, halogen, trifluoromethyl, nitro, amino, hydroxy and $C_1-C_4$ alkoxy;
    (d) a group $—COR_5$ wherein $R_5$ is
      (i) a $C_1-C_{22}$ saturated or $C_2-C_{22}$ unsaturated aliphatic hydrocarbon radical;
      (ii) a $C_4-C_7$ monocycloalkyl group; or
      (iii) a phenyl or benzyl group, each unsubstituted or ring substituted as reported above; or
    (e) a hydroxy protecting group;
  (2) a group $—SR_6$ wherein $R_6$ either has one of the meanings (a) to (d) indicated above for $R_4$ or is a group $—SR_7$ wherein $R_7$ is
    (iv) $C_1-C_6$ alkyl;
    (v) a phenyl or benzyl group, each unsubstituted or ring-substituted as reported above; or
    (vi) a steroidic residue of formula

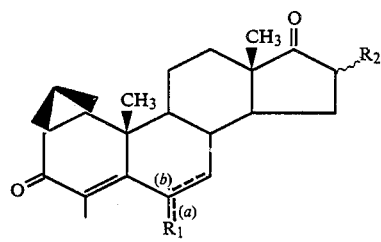

wherein $R_1$, $R_2$, (a), (b) and the symbol  are as defined above;
  (3) the group $—N_3$; or
  (4) a group $$-N\begin{matrix}R_8\\R_9\end{matrix}$$

wherein each of $R_8$ and $R_9$, independently, is hydrogen or $C_1-C_6$ alkyl, and the pharmaceutically acceptable salts thereof.

2. A compound of formula (I) according to claim 1 wherein R is
  (1) a group $—OR'_4$ wherein $R'_4$ is hydrogen, $C_1-C_6$ alkyl or a group $—COR'_5$ wherein $R'_5$ is a $C_1-C_{22}$ saturated aliphatic hydrocarbon radical; or
  (2) a group $—SR'_6$ wherein $R'_6$ has the meanings reported above for $R'_4$;
  $R_2$ is hydrogen or fluorine; and
  either (i) $R_1$ is hydrogen, (a) is single bond and (b) is single or double bond,
  or (ii) $R_1$ is a group $=CHR_3$ wherein $R_3$ is hydrogen, (a) is double bond and (b) is single bond.

3. A compound of formula (I) according to claim 1 wherein
R is a group $$-N\begin{matrix}R_8\\R_9\end{matrix}$$

wherein each of $R_8$ and $R_9$, independently, is hydrogen or $C_1-C_6$ alkyl;
$R_2$ is hydrogen or fluorine; and either
  (i) $R_1$ is hydrogen, (a) is single bond and (b) is single or double bond, or
  (ii) $R_1$ is a group $=CHR_3$ wherein $R_3$ is hydrogen, (a) is double bond and (b) is single bond,
and the pharmaceutically acceptable salts thereof.

4. A compound of formula (I) according to claim 1 selected from the group consisting of:

1,2β-methylene-4-hydroxyandrost-4-ene-3,17-dione;
1,2β-methylene-4-hydroxy-16α-fluoroandrost-4-ene-3,17-dione;
1,2β-methylene-4-hydroxy-16β-fluoroandrost-4-ene-3,17-dione;
1,2β-methylene-4-hydroxy-6-methylenandrost-4-ene-3,17-dione;
1,2β-methylene-4-hydroxy-6-methylene-16α-fluoroandrost-4-ene-3,17-dione;
1,2β-methylene-4-hydroxy-6-methylene-16β-fluoroandrost-4-ene-3,17-dione;
1,2β-methylene-4-hydroxyandrosta-4,6-diene-3,17-dione;
1,2β-methylene-4-hydroxy-16β-fluoroandrosta-4,6-diene-3,17-dione;
1,2β-methylene-4-hydroxy-16α-fluoroandrosta-4,6-diene-3,17-dione;
1,2β-methylene-4-methoxyandrost-4-ene-3,17-dione;
1,2β-methylene-4-methoxy-16α-fluoroandrost-4-ene-3,17-dione;
1,2β-methylene-4-methoxy-16β-fluoroandrost-4-ene-3,17-dione;
1,2β-methylene-4-methoxy-6-methylenandrost-4-ene-3,17-dione;
1,2β-methylene-4-methoxy-6-methylene-16α-fluorandrost-a4-ene-3,17-dione;
1,2β-methylene-4-methoxy-6-methylene-16β-fluoroandrost-4-ene-3,17-dione;
1,2β-methylene-4-methoxyandrosta-4,6-diene-3,17-dione;
1,2β-methylene-4-methoxy-16β-fluoroandrosta-4,6-diene-3,17-dione;
1,2β-methylene-4-methoxy-16α-fluoroandrosta-4,6-diene-3,17-dione;
1,2β-methylene-4-acetoxyandrost-4-ene-3,17-dione;
1,2β-methylene-4-acetoxy-16α-fluoroandrost-4-ene-3,17-dione;
1,2β-methylene-4-acetoxy-16β-fluoroandrost-4ene-3,17-dione;
1,2β-methylene-4-acetoxy-6-methylenandrost-4-ene-3,17-dione;
1,2β-methylene-4-acetoxy-6-16α-fluoroandrost-4-ene-3,17-dione;
1,2β-methylene-4-acetoxy-6-methylene-16β-fluoroandrost-4-ene-3,17-dione;
1,2β-methylene-4-acetoxyandrosta-4,6-diene-3,17-dione;
1,2β-methylene-4-acetoxyandrosta-4,6-diene-3,17-dione;
1,2β-methylene-4-acetoxy-16α-fluoroandrosta-4,6-diene-3,17-dione;
1,2β-methylene-4-mercaptoandrost-4-ene-3,17-dione;
1,2β-methylene-4-mercapto-16α-fluoroandrost-4-ene-3,17-dione;
1,2β-methylene-4-mercapto-16β-fluoroandrost-4-ene-3,17-dione;
1,2β-methylene-4-mercapto-6-methylenandrost-4-ene-3,17-dione;
1,2β-methylene-4-mercapto-6-methylene-16α-fluoroandrost-4-ene-3,17-dione;
1,2β-methylene-4-mercapto-6-methylene-16β-fluoroandrost-4-ene-3,17-dione;
1,2β-methylene-4-mercaptoandrosta-4,6-diene-3,17-dione;
1,2β-methylene-4-mercapto-16β-fluoroandrosta-4,6-diene-3,17-dione;
1,2β-methylene-4-mercapto-16α-fluoroandrosta-4,6-diene-3,17-dione;
1,2β-methylene-4-acetylthioandrost-4-ene-3,17-dione;
1,2β-methylene-4-acetylthio-16α-fluoroandrost-4-ene-3,17-dione;
1,2β-methylene-4-acetylthio-16β-fluoroandrost-4-ene-3,17-dione;
1,2β-methylene-4-acetylthio-6-methylenandrost-4-ene-3,17-dione;
1,2β-methylene-4-acetylthio-6-methylene-16α-fluoroandrost-4-ene-3,17-dione;
1,2β-methylene-4-acetylthio-6-methylene-16β-fluoroandrost-4-ene-3,17-dione;
1,2β-methylene-4-acetylthioandrosta-4,6-diene-3,17-dione;
1,2β-methylene-4-acetylthio-16β-fluoroandrosta-4,6-diene-3,17-dione;
1,2β-methylene-4-acetylthio-16α-fluoroandrosta-4,6-diene-3,17-dione;
1,2β-methylene-4-methylthioandrost-4-ene-3,17-dione;
1,2β-methylene-4-methylthio-16α-fluoroandrost-4-end-3,17-dione;
1,2β-methylene-4-methylthio-16β-fluoroandrost-4-ene-3,17-dione;
1,2β-methylthio-6-methylenandrost-4-ene-3,17-dione;
1,2β-methylene-4-methylthio-6-methylene-16α-fluoroandrost-4-ene-3,17-dione;
1,2β-methylene-4-methylthio-6-methylene-16β-fluoroandrost-4-ene-3,17-dione;
1,2β-methylene-4-methylthioandrosta-4,6-diene-3,17-dione;
1,2β-methylene-4-methylthio-16β-fluoroandrosta-4,6-diene-3,17-dione;
1,2β-methylene-4-methylthio-16α-fluoroandrosta-4,6-diene-3,17-dione,
1,2β-methylen-4-aminoandrost-4-ene-3,17-dione;
1,2β-methylen-4-amino-16α-fluoroandrost-4-ene-3,17-dione;
1,2β-methylen-4-amino-16β-fluoroandrost-4-ene-3,17-dione;
1,2β-methylen-4-amino-6-methylenandrost-4-ene-3,17-dione;
1,2β-methylen-4-amino-6-methylene-16α-fluoroandrost-4-ene-3,17-dione;
1,2β-methylen-4-amino-6-methylene-16β-fluoroandrost-4-ene-3,17-dione;
1,2β-methylen-4-aminoadrosta-4,6-diene-3,17-dione;
1,2β-methylen-4-amino-16β-fluoroandrosta-4,6-diene-3,17-dione;
1,2β-methylen-4-amino-16α-fluoroandrosta-4,6-diene-3,17-dione;
and the pharmaceutically acceptable salts thereof.

* * * * *

UNITED STATES PATENT AND TRADEMARK OFFICE
CERTIFICATE OF CORRECTION

PATENT NO. : 4,810,423

DATED : March 7, 1989

INVENTOR(S) : BUZZETTI et al

It is certified that error appears in the above-identified patent and that said Letters Patent is hereby corrected as shown below:

On the cover page, Item [57], line 3 of the ABSTRACT, the formula should appear as follows:

-- 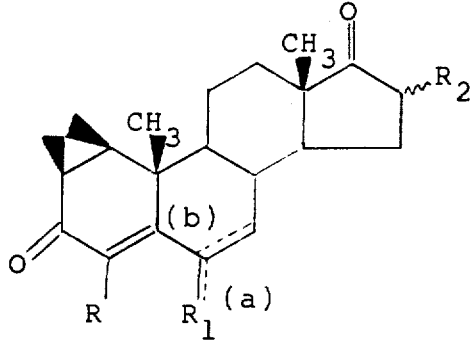 --;

line 32 of the ABSTRACT, the formula should appear as follows:

-- 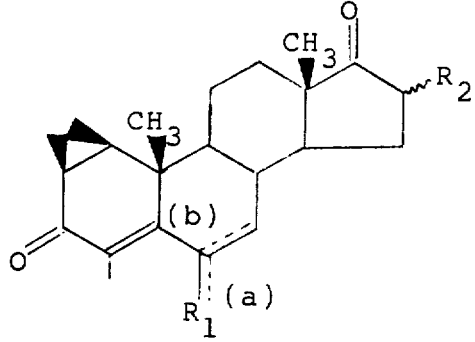 --.

UNITED STATES PATENT AND TRADEMARK OFFICE
CERTIFICATE OF CORRECTION

PATENT NO. : 4,810,423
DATED : March 7, 1989
INVENTOR(S) : BUZZETTI et al

It is certified that error appears in the above-identified patent and that said Letters Patent is hereby corrected as shown below:

Column 1, lines 50 to 59, the formula should appear as follows:

-- 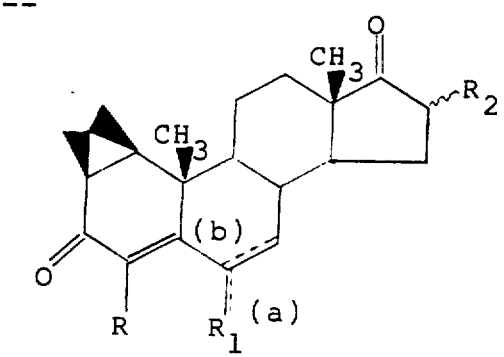 --.

Column 2, lines 21 to 30, the formula should appear as follows:

-- 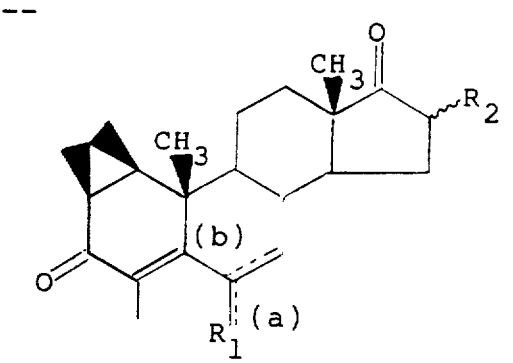 --.

UNITED STATES PATENT AND TRADEMARK OFFICE
CERTIFICATE OF CORRECTION

PATENT NO. : 4,810,423

DATED : March 7, 1989

INVENTOR(S) : BUZZETTI et al

It is certified that error appears in the above-identified patent and that said Letters Patent is hereby corrected as shown below:

Column 10, lines 55 to 64, the formula should appear as follows:

-- 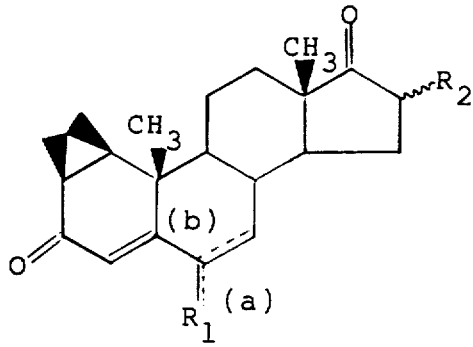 --.

Column 19, lines 45 to 54, the formula should appear as follows:

-- 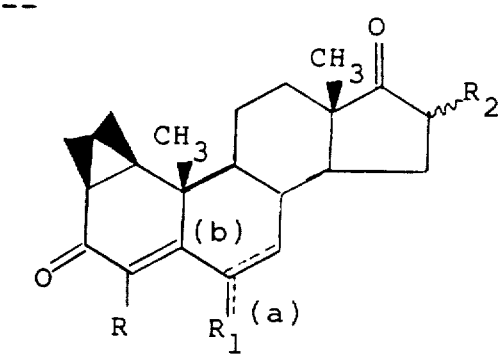 --.

UNITED STATES PATENT AND TRADEMARK OFFICE
CERTIFICATE OF CORRECTION

PATENT NO. : 4,810,423
DATED : March 7, 1989
INVENTOR(S) : BUZZETTI et al

It is certified that error appears in the above-identified patent and that said Letters Patent is hereby corrected as shown below:

Column 20, lines 15 to 25, the formula should appear as follows:

-- 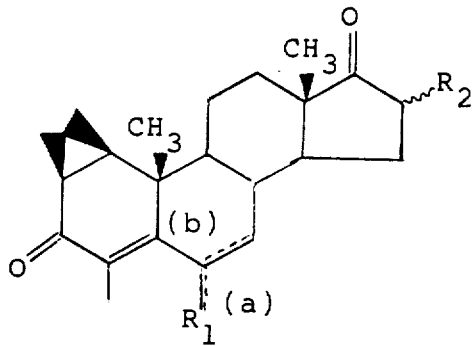 --.

UNITED STATES PATENT AND TRADEMARK OFFICE
CERTIFICATE OF CORRECTION

PATENT NO. : 4,810,423
DATED : March 7, 1989
INVENTOR(S) : Buzzetti, et al

It is certified that error appears in the above-identified patent and that said Letters Patent is hereby corrected as shown below:

Column 21, lines 45 and 46, "1,2β-methylene-4-acetoxy-6-16α-fluoroandrost-4-ene-3,17-dione" should read --1,2β-methylene-4-acetoxy-6-methylene-16α-fluoroandrost-4-ene-3-17-dione--;

lines 51 and 52, "1,2β-methylene-4-acetoxyandrosta-4,6-diene-3,17-dione" should read --1,2β-methylene-4-acetoxy--16β-fluorandrosta-4,6-diene-3,17-dione--.

Signed and Sealed this

Twenty-first Day of May, 1991

Attest:

HARRY F. MANBECK, JR.

Attesting Officer

Commissioner of Patents and Trademarks